United States Patent
Andrieu et al.

(10) Patent No.: US 7,347,870 B1
(45) Date of Patent: Mar. 25, 2008

(54) DEVICE FOR SHRINKING OR REINFORCING THE HEART VALVULAR ORIFICES

(75) Inventors: Raymond Andrieu, Yens (CH); Philippe Le Goff, Le Mont-sur-Lausanne (CH); Afksendiyos Kalangos, Geneva (CH)

(73) Assignees: Bioring SA, Lonay (CH); Afksendiyos Kalangos, Geneva (CH)

( * ) Notice: Subject to any disclaimer, the term of this patent is extended or adjusted under 35 U.S.C. 154(b) by 481 days.

(21) Appl. No.: 10/296,449

(22) PCT Filed: Nov. 7, 2000

(86) PCT No.: PCT/IB00/01605

§ 371 (c)(1),
(2), (4) Date: Jul. 11, 2003

(87) PCT Pub. No.: WO01/89426

PCT Pub. Date: Nov. 29, 2001

(30) Foreign Application Priority Data

May 25, 2000 (WO) .......................... PCTIB0000707

(51) Int. Cl.
*A61F 2/06* (2006.01)
(52) U.S. Cl. .................................................. 623/2.36
(58) Field of Classification Search ............... 623/1.11, 623/2.36–2.41
See application file for complete search history.

(56) References Cited

U.S. PATENT DOCUMENTS

| 3,463,158 | A | * | 8/1969 | Schmitt et al. ............. 606/154 |
| 4,917,698 | A |   | 4/1990 | Carpentier et al. |
| 4,923,470 | A |   | 5/1990 | Dumican |
| 5,792,400 | A | * | 8/1998 | Talja et al. ................. 264/103 |

FOREIGN PATENT DOCUMENTS

| EP | 0 338 994 | 10/1989 |
| EP | 0 594 148 | 4/1994 |
| WO | 96 04852 | 2/1996 |
| WO | 97 16135 | 5/1997 |

* cited by examiner

*Primary Examiner*—William H. Matthews
(74) *Attorney, Agent, or Firm*—Young & Thompson

(57) ABSTRACT

A device for shrinking and/or reinforcing the heart valve orifices includes a thick link (1) made of a bioresorbable, soft and curved material. It is secured at one of its ends to at least a thin yarn (3) whereof the end is fixed to a curved needle.

2 Claims, 4 Drawing Sheets

DEVICE FOR SHRINKING OR REINFORCING THE HEART VALVULAR ORIFICES

Lesions of the valvular orifices of the heart, whether of the sigmoidal valvules of the aorta or of the pulmonary artery or mitral or tricuspidal valves, occur in 80 to 90% of the cases of a prolapsis or restriction which lead to dilation of the ring by enlarging the cardiac cavities in question and in practically all the rest of the cases a dilation of the ring without associated valvular lesions.

After correction of the associated valvular lesions, it is necessary to correct at the same time the dilation of the valvular ring and to hold it in its normal dimension. To prevent recurrence of such lesions, it is necessary to reinforce the ring surrounding the valvular orifices.

To carry out such repairs of the valvular orifices, there have been proposed several types of rigid or flexible implants having the general shape of rings, such as the DURAN, CARPENTIER or PUIG-MASSANA rings, or segments such as that of COSGROVE. These rigid or flexible rings or segments or disposed and stitched along the periphery of the ring of the valvular orifice to be repaired. The opening of the valvular orifice is thus brought to the desired dimension, generally calculated in proportion to the surface of the body of the patient, and maintained in this normal dimension.

The document EP 0 338 994 discloses such a device for the surgical correction of tricuspidal insufficiency, adapted to be fixed, specifically stitched, along the periphery of the ring of the valvular orifice to be repaired, this usually on the internal surface of this valvular orifice. So as to accelerate the process of securement by suturing, this device can be provided at its ends with a filament and a needle. This filament and corresponding needle however serve no other purpose than more rapid suturing, once the insertion of the device in the heart has been completed, and the device thus remains in the context of known implants and implantation techniques by improving only the speed of a conventional surgical procedure.

These implanted rings are generally of synthetic material or metal and can predispose certain patients to valvular infections in the case of bacteria, requiring therapeutical, curative and preventive treatments and, as the case may be, a new intervention.

Moreover, when these rigid or flexible rings are used in babies, they prevent normal growth of the ring of the valvular orifice in question, which leads to stenoses and also to one or several new interventions to enlarge the ring and replace the stenoses and also to one or several new successive interventions to enlarge the ring and to replace the stenotic valve.

The document WO 97/16135 discloses a resorbable annular cardiac prosthesis. The ring disclosed in this document is formed of a biodegradable material so as to permit the replacement of this material by biological material belonging to the patient during the resorption period. However, this ring is also adapted to be disposed in a conventional manner on the internal surface of the valvular orifice along the periphery of the ring of this valvular orifice to be repaired.

The present invention has for its object a device to contract and/or to reinforce the valvular orifices of the heart which avoids any predisposition to infection and which permits the normal growth of the ring of the valve in infants, thereby avoiding stenoses or successive interventions; moreover, the device is arranged so as to permit a surgical procedure altogether new and innovative and thus improves greatly the speed, the facility and the applicability of the surgical procedure.

The device to contract and/or reinforce the valvular orifices of the heart is distinguished by the characteristics set forth in claim 1 and/or claim 2.

The accompanying drawings show schematically and by way of example several embodiments of the device according to the invention.

Figure 1:
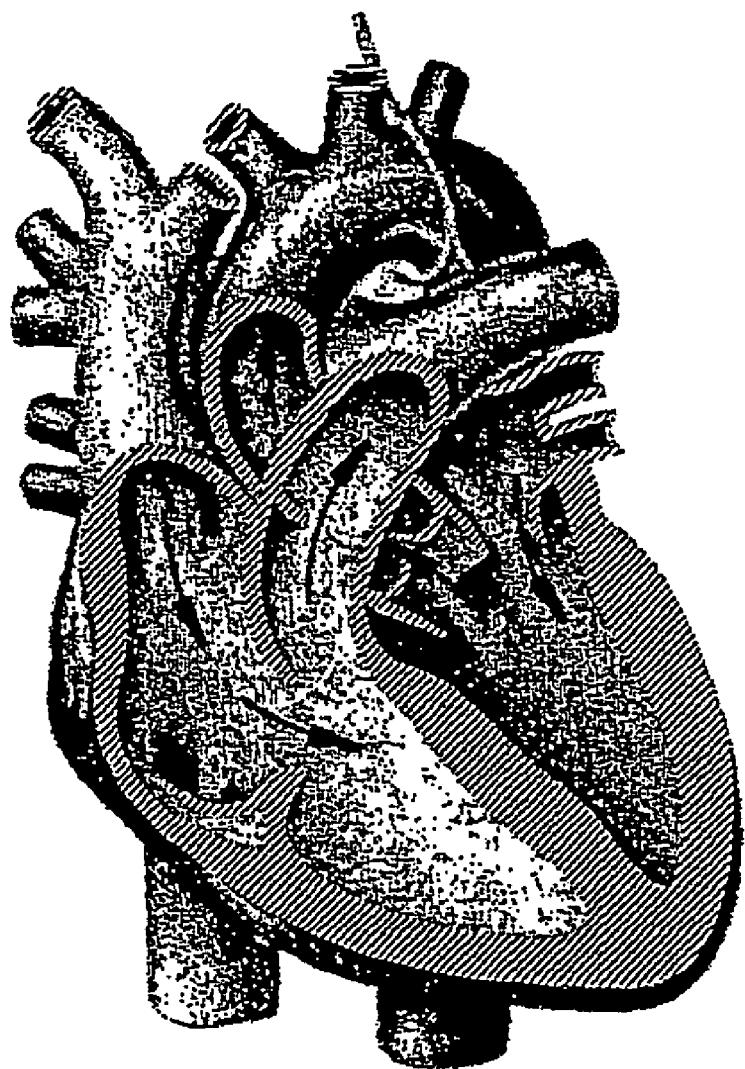
FIG. 1 is a schematic representation of the human heart.

In place of rigidly and/or definitively fixing a rigid or flexible ring or segment along all or a part of the periphery of the valvular orifice, as was done until now, the present technique consists in arranging a flexible connection along all or a part of the periphery of the valvular orifice at the interior of the endocardium, namely the layer of tissue located on the internal side of the myocardial muscle, to define the dimension of the valvular opening by a length defined by the connection, to fix the latter at one or two points of the endocardium for example by points of suturing.

Moreover, in the present technique, there is utilized a resorbable connection (biodegradable or bioabsorbable) which is to say biodegradable and not giving rise to an immune response on the part of the organism. In what follows of this paper, the term resorbable will be used to define either bioabsorbable or biodegradable and the suture filaments resorbable or not. In a first instance after the operation, the connection holds the valvular ring at its normal or desired dimension, thereby preventing its dilation.

Then, by the action of resorption of the connection within the endomicardial layer, the organism creates, by reaction, a scar along the connection characterized by fibrous tissue having a greater resistance to stretching. Thus, once the connection is resorbed by the organism, folding the valvular orifice at the desired dimension is effected by the rigidity of this fibrous tissue of the scar.

Because the residual scar is constituted of biological tissues belonging to the patient, there is no predisposition to infection, but above all this scar can increase normally in the course of the process of growth of the infant, which avoids problems of late stenoses.

This new technique is rendered possible by the device for repairing lesions, for contraction and/or reinforcement of the valvular orifices of the heart according to the present invention. In a first embodiment, this device comprises a connection 1, made of a material resorbable by the organism, terminating at one of its ends in a loop 2 or a stop member and of resorbable securement or not, for example a hook or barb permitting the securement of this end to the endomiocardium. The other end of the connection 1 is secured, generally made of one piece during manufacture, to a thin filament 3 that is very flexible, such as a suturing filament. This thin filament 3 is preferably also resorbable and generally formed of the same material as the connection 1.

This filament 3 is fixed at its free end to a needle 4 permitting emplanting the connection 1 of the device.

It is evident that the present device is made in several sizes because for easy emplacement, it is preferable that the curve and the length of the needle 4 correspond to the curve of the ring of the valvular orifice and to the length of the portion of perimeter of the orifice that is to be provided with the connection 1 of the device.

Similarly, it is preferable that the connection 1 have a length and if possible a curve corresponding to the portion of the periphery of the valvular orifice to be provided with the connection.

Figure 2:
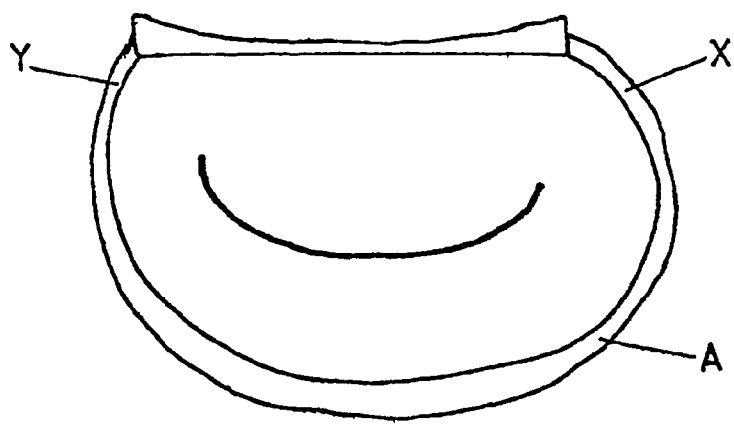
FIGS. 2, 3 and 4 are simplified schematics showing respectively the mitral valve, the tricuspid valve and the sigmoidal valves.
Figure 3:
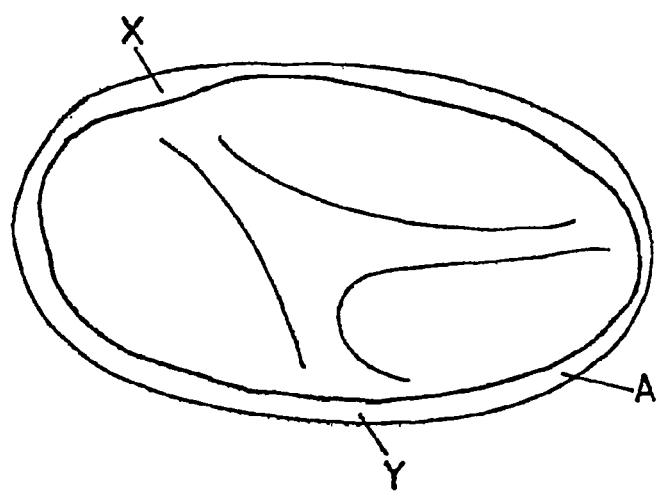
Figure 4:
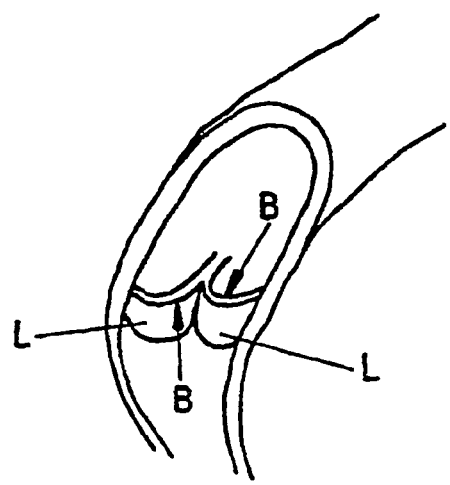
Figure 5:
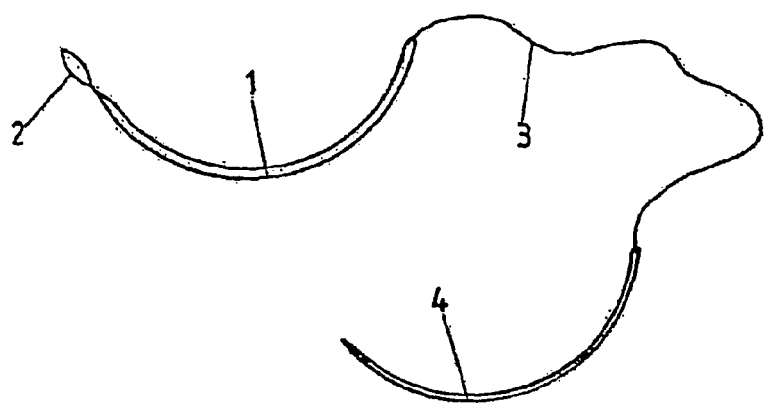
FIG. 5 shows in a schematic or simplified way a first embodiment of the device according to the invention.

Thus the surgeon can, in the case of the valves shown in FIGS. 2 and 3, introduce the needle 4 at X into the endomiocardium of the valvular ring A, pass the needle within this layer of tissue to point Y of the valvular ring A, because the curve of the needle 4 and its length are adapted to the valve which is to be equipped therewith.

The surgeon brings out the needle 4 at the point Y and draws the filament 3 to move the connection 1 into position in which the securement member 2 is located adjacent the point of introduction X and the junction between the connection 1 and the thin filament 3 is itself located at the exit point Y. The surgeon fixes by taking several suture points and by if desired using a stop, for example a button, the connection 1 to the exit point Y with the filament 3, then cuts this filament 3. Finally, the surgeon fixes and buries in the endomiocardium by several suture points the loop 2 or the stop provided at the free end of the connection 1.

It is also possible to provide all the perimeter of the valvular ring with a connection 1. In this case, the points X and Y are near each other or coincide and the filaments 3 at the two ends of the connection 1 are knotted together, cut and buried in the endomiocardium.

The connection 1 has a curvature corresponding approximately to that of the ring of the orifice of the valve and the quantity of resorbable material depends on the mass of fibrous tissues which it is desired to induce by resorption to obtain the desired rigidity of this natural scar which over the long term alone will ensure the holding of the ring of the orifice of the valve and prevent any dilation of the latter.

Several sizes of the device are provided as a function of the diameter of the valvular orifice and of the body surface of the patient, the connection 1 and the needle 4 depending on this diameter and on the portion X-Y of the periphery of the valvular orifice to be outfitted. Moreover, for each of the sizes, several types are provided with different thicknesses of the connection 1. In a modification of the described device, the connection 1 of resorbable material is clad with a layer of a second material more rapidly resorbable than that used to make the internal portion of the connection. In this way, there is obtained by the resorption of this layer or cladding, an initial rapid resorption, for example over several days to several weeks, and hence the more rapid formation of fibrous tissue permitting quasi-immediate reinforcement of the valvular orifice. This initial rapid scar formation is followed by a slow scar formation, six to twelve months, due to the resorption of the central portion of the connection 1.

To determine the size of the device to be used, the surgeon has testers, templates of the shape of the valvular orifices, but of different cross-sections. By selecting a tester corresponding to the size of the surface of the anterior flap of the mitral or tricuspidal valve to be repaired or to the diameter of the sinotubular junction where the three sigmoidal valvules coapt, the surgeon determines the size of the device to be used. The choice of the type of device within the predetermined size is made as a function of the age of the patient, of the body surface, and of the condition of the lesion. The greater the quantity of resorbable material of the connection 1, the larger will be the scar and the stronger will be the reinforcement of the ring of the valvular orifice.

Figure 6:
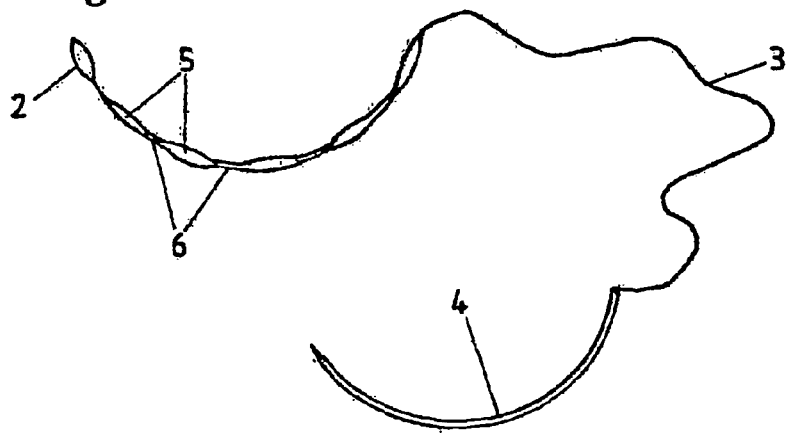
FIG. 6 shows in a schematic or simplified way a second embodiment of the device according to the invention.

In the second embodiment of the device shown in FIG. 6, the connection has a series of enlargements 5 and of thinned portions 6. This type of device gives rise to light or weak scarring at the thinned portions 6 and strong scarring at the enlargements 5. This is particularly interesting in young infants or babies because during growth of the weakly scarred portions, corresponding to the thinned portions 6, these can easily stretch as a function of the growth of the subject.

Here again, it is preferable that the curvature of the needle 4 and that of the resorbable connection 5, 6 correspond substantially to that of the valvular orifice to be thus equipped.

In this embodiment also, the resorbable connection 5, 6 can be covered with a layer of more rapidly resorbable material than that used to make the interior of the connection, so as to create a two-stage resorption.

Figure 7:
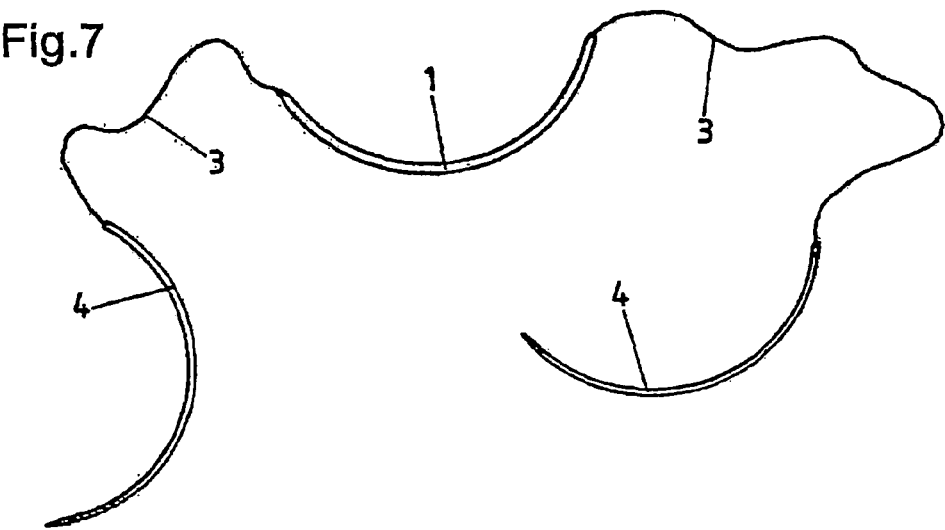
FIG. 7 shows in a schematic or simplified way a third embodiment of the device according to the invention.

The third embodiment of the device shown in FIG. 7 is more particularly, but not exclusively, adapted for the case of repair, contraction or reinforcement of valvular orifices in which it is necessary to reinforce all the periphery of the valvular orifice, for example in the case of the mitral, tricuspid and sigmoidal valves.

This device comprises a thick and resorbable connection 1 whose ends both comprise thin filaments 3 each one provided with a needle 4.

Figure 9:
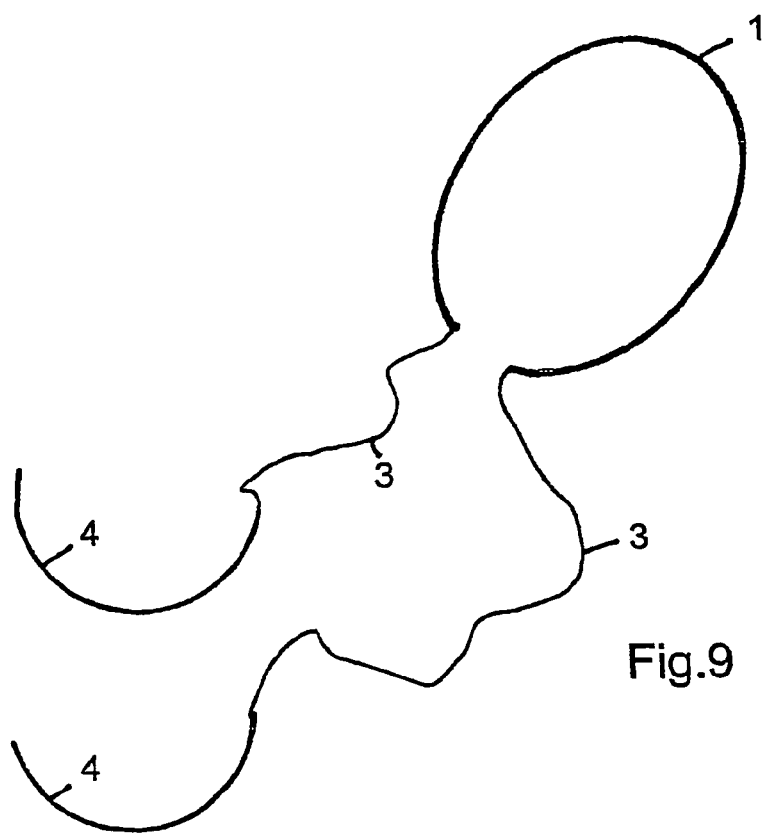
FIG. 9 shows in a schematic or simplified way a modification of the device shown in FIG. 7.

With the help of one or the other needle 4, the surgeon introduces the resorbable connection 1 into the endomiocardium so as to form a loop then he knots the two thin filaments 3, also resorbable, of the device so as to hold the connection 1 closed on itself. The rest of the filament is cut away (see FIG. 9).

Here again, the curvature of the needles 4 and the connection 1 of the device correspond preferably to the nominal curvature of the valvular orifice to be treated.

Of course, the connection 1 can comprise, as shown in FIG. 6, enlargements and thin portions. Similarly, this connection 1 can comprise a layer or a cladding made of a more rapidly resorbable material than that forming the interior of the connection 1 of the device, so as to obtain two-stage resorption.

Figure 8:
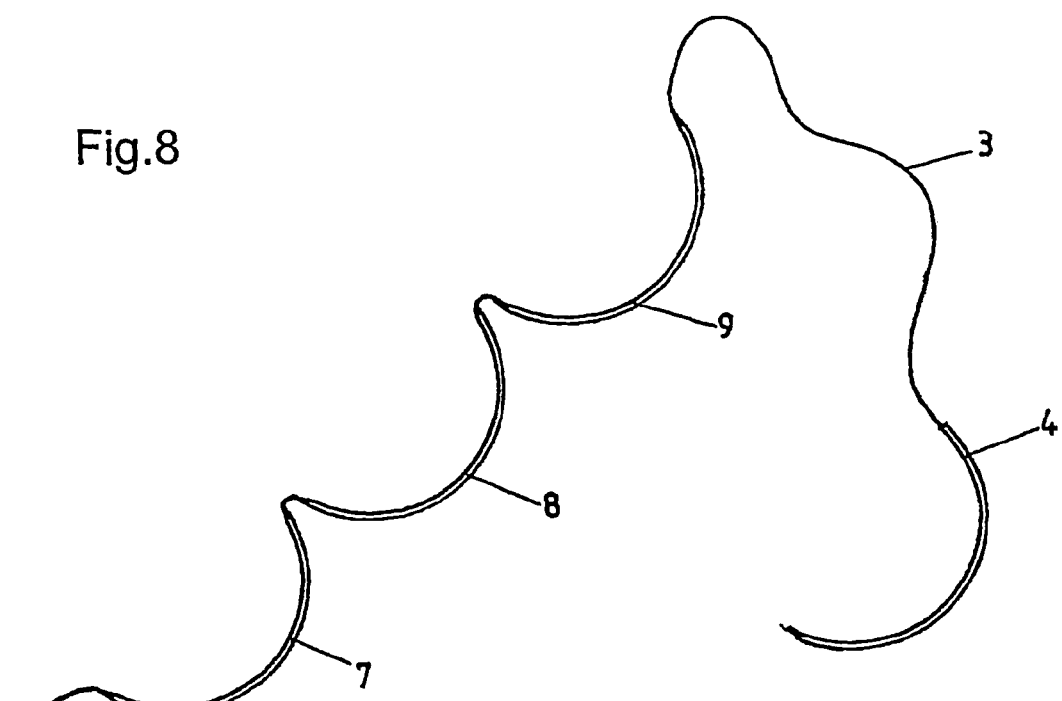
FIG. 8 shows in a schematic or simplified way a fourth embodiment of the device according to the invention.

The fourth embodiment of the device according to the invention, shown in FIG. 8, is more particularly adapted to the repair of sigmoidal valves formed of three lobes L.

In this embodiment, the connections constituted by several, in this case three, portions 7, 8, 9. The central portion 8 is connected to the lateral portions 7, 9 of this central portion and these lateral portions each comprise a filament 3 terminating in a needle 4.

The curvature of the needles 4 and of the portions 7, 8, 9 of the connection correspond to the curvature of the free edges B of the lobes L of the sigmoidal valve. With the help of needles 4, there is introduced into the endomiocardium along the edges B of the lobes L of the valvule, the portions 7, 8, 9 such that each of them corresponds to a lobe L.

The filaments 3 are then knotted together and cut.

Here again, the connection and possibly the filaments 3 are of a resorbable material, if desired two-stage as described above.

The principal advantages of the device described are as follows:

absence of predisposition to infection because the implanted connection is biologically resorbable.

facility of emplacement of the connection because its shape and the shape of the needles, is adapted to the curve of the valvular orifice. Thus, this permits entering into the endomiocardium at a place and leaving it at another place or at the same place, without intermediate perforation.

the possibility of creating resorption in two stages.

the possibility of creating distributions reinforcing the ring of the valvular orifice and avoiding dilation whilst permitting this valvular ring to grow as a function of the growth of the subject, which avoids late stenoses.

Numerous variations can be envisaged, particularly as to the shape and composition of the device and more particularly to its thick portion of the connection.

This connection can have a diameter of the order of 0.2 mm to several millimeters, according to the conditions of use. Its cross-section may be circular, oval, polygonal and particularly rectangular to give it a greater resistance to deformation. This connection is generally flexible, but returns by its natural elasticity to its curved shape corresponding approximately to that of the valvular orifice.

One of the novel characteristics of the invention consists in using one or several resorbable materials for the production of the connection 1 and its filaments 3. Thus, if the resorbable materials are known for various applications in the field of medical devices, for example as suture filaments, or as prostheses, or else as devices for the controlled release of medicinal substances into the organism, there exists no application in which the material has to ensure, in addition to its primary function of a repair element, a function of inducing a curative and evolutive action from the organism itself.

The resorbable materials finding application in the fields of health are obtained from tissues or proteins from the animal kingdom, such as collagen or catgut, or from polymers produced synthetically.

The chemical nature of the principal polymers known to be resorbable, include polyesters, polyorthoesters, polyanhydrides, poly(ether)esters, polyaminoacids and polydepsipeptides (see for example: B. Buchholz; J. Mater. Sci. Mater: Med. 4 (1993) 381-388).

More schematically, but not exclusively, the resorbable polymers can be described by a structure corresponding to the general formula:

—[—X1-C(O)—R1-Y1-R2-]—[—X2-C(O)—R3-Y2-R4-]— in which:

C(O) designates a >C=O group,

X1; X2 designate an oxygen atom or an NH group,

Y1 (respectively Y2) designates an oxygen atom, or an NH group, or a chemical connection directly connecting R1 to R3) respectively R2 to R4), R1; R2; R3; R4 designate linear or branched carbon chains, saturated or partially unsaturated, bearing or not hetero atoms and containing 0 to 10 carbon atoms.

When in this general formula, X1 is equal to X2 and Y1 is equal to Y2 and R1 is equal to R3 and R2 is equal to R4, the obtained polymer is called a homopolymer. In the contrary case, the polymer obtained is called a copolymer.

Among these polymers, the inventors have focused attention on the polymers that can be described by a structure responding to a general formula: —[—X1-C(O)—R1-Y1-R2-]—[—X2-C(O)—R3-Y2-R4-]—

In which:

C(O) designates a >C=O group,

X1; X2 designates an oxygen atom,

Y1 (respectively Y2) designates an oxygen atom or a chemical bond directly connecting R1 to R3 (respectively R2 to R4), R1; R2; R3; R4 designate linear or branched carbon chains and contain 0 to 5 carbon atoms and preferably 0 to 3 atoms.

These types of polymers include for example polylactides, polyglycolides, polydioxanones, polyalkylenecarbonates, and polylactones. To these homopolymers must be further added the copolymers obtained by a combination of the different monomers.

These polymers are known for their ability to be resorbed in vivo according to known and predictable modes of resorption.

Moreover, among these polymers, certain have particularly interesting characteristics to enter into the production of the device as described in claim 1.

Thus, for example, the polydioxanones are known to resorb more slowly than the polylactides, or the polyglycolides, or else catgut or collagen.

On the other hand, the flexibility of the material obtained also depends on the nature of the polymer used. The mechanical characteristics of the obtained material will vary for example with the chemical nature of the structure, the molecular weight, the polymerization process, the technique of using the material, . . .

Optimization of the different parameters bearing on the characteristics of the obtained material, has resulted in a preference for polydioxanones to produce the connection 1. The polydioxanones are polymers obtained from cyclic monomers having the general formula $C_4H_6O_3$ and have a >C=O group. They offer in vivo resorption kinetics compatible with the formation of scar mass and can be developed with the mechanical characteristics necessary for their use.

In the case in which the connection 1 is formed by two different materials, it can be provided that the latter comprises an internal portion of polydioxanone and an external cladding made of a more rapidly resorbable polymer. The external cladding gives rise to a first fibrous reaction during its early resorption whilst protecting the polydioxanone which will begin its slow resorption only when the external cladding has been resorbed. There is thus obtained a more tardy resorption which leads to more consolidated fibrous reaction.

In the case in which the connection comprises enlargements and thinned portions, the principal thick segments 5 will comprise the two materials whilst the thin connection portions 6 could comprise only one of the two mentioned materials.

Instead of using monofilament material for the connection, there can be used woven or multi-fibrous materials.

What is claimed is:

1. Process for repair of a valvular orifice with the help of a device for contracting and/or reinforcing valvular orifices of a heart, the device comprising a thick connection (1) of a resorbable material, flexible and curved, secured at one of its ends to at least one thin filament (3) whose end is fixed to a curved needle (4), the filament (3) being arranged such that it permits exerting a longitudinal traction on the thick connection (1) in the direction of a longitudinal axis of this thick connection (1), this longitudinal traction being adapted to allow the thick connection (1) to be introduced inside the tissue of the valvular orifice to be treated, according to which process the needle is introduced into the endomiocardium of the valvular ring, caused to follow in the latter a path over a portion of the periphery of the valvular orifice whilst always remaining in the endomiocardium, the needle exits from the endomiocardium at a point of extraction and moves, with the help of the filament exerting a longitudinal traction on the connection in the direction of the longitudinal axis of this connection, the connection into the endomiocardium such that its free end will be located at the point of introduction; this end of the connection is then fixed to the endomiocardium; the connection is caused to slide inside the ring of the valvular orifice until its other end is located at the point of extraction from the endomiocardium; then this second end of the connection is fixed to the endomiocardium and the filament is cut.

2. Process according to claim 1, characterized by the fact that the points of extraction and removal are adjacent each other or coincident and that the filaments fixed to each of the ends of the connection are knotted together and then cut.

* * * * *